(12) United States Patent
Gaitan et al.

(10) Patent No.: US 8,715,591 B2
(45) Date of Patent: May 6, 2014

(54) MICROFLUIDIC APPARATUS TO CONTROL LIPOSOME FORMATION

(75) Inventors: Michael Gaitan, Gaithersburg, MD (US); Andreas Jahn, Zürich (CH); Laurie E. Locascio, Gaithersburg, MD (US); Wyatt Vreeland, Gaithersburg, MD (US); Joseph E. Reiner, Fredericksburg, VA (US)

(73) Assignee: The United States of America, as represented by the Secretary of Commerce, the National Institute of Standards and Technology, Washington, DC (US)

( * ) Notice: Subject to any disclaimer, the term of this patent is extended or adjusted under 35 U.S.C. 154(b) by 739 days.

(21) Appl. No.: 12/762,794

(22) Filed: Apr. 19, 2010

(65) Prior Publication Data

US 2010/0202928 A1 Aug. 12, 2010

Related U.S. Application Data

(63) Continuation-in-part of application No. 10/895,366, filed on Jul. 21, 2004.

(60) Provisional application No. 61/172,806, filed on Apr. 27, 2009.

(51) Int. Cl.
*B01L 3/00* (2006.01)
(52) U.S. Cl.
USPC .......................................................... 422/502
(58) Field of Classification Search
None
See application file for complete search history.

(56) References Cited

U.S. PATENT DOCUMENTS

| 5,486,335 | A | * | 1/1996 | Wilding et al. | 422/400 |
|---|---|---|---|---|---|
| 6,454,945 | B1 | * | 9/2002 | Weigl et al. | 210/634 |
| 6,596,305 | B1 | | 7/2003 | Edgerly-Plug | |
| 7,595,195 | B2 | | 9/2009 | Lee et al. | |
| 2004/0121450 | A1 | * | 6/2004 | Pugia et al. | 435/287.1 |
| 2005/0032240 | A1 | | 2/2005 | Lee et al. | |

FOREIGN PATENT DOCUMENTS

CA  WO2004002453  *  1/2004

OTHER PUBLICATIONS

Andreas Wagner et al., Enhanced Protein Loading into Liposomes by the Multiple Crossflow Injection Technique, J. Liposome Research 12 (3), 271-283 (2002).
Yang H. et al., Sample Stacking in Laboratory-on-a-chip Devices, J. Chromatography A 924 (1), 155-163 (2001).
Anette Stromberg et al., Microfluidic Device for Combinatorial Fusion of Liposomes and Cells, Anal. Chem. 73 (1), 126-130 (2001).
Paul J. A. Kenis et al., Microfabrication Inside Capillaries Using Multiphase Laminar Flow Patterning, Science 285, 83-85 (1999).

* cited by examiner

*Primary Examiner* — Brian Gulledge
*Assistant Examiner* — Snigdha Maewall
(74) *Attorney, Agent, or Firm* — Absolute Technology Law Group, LLC

(57) ABSTRACT

An apparatus to create a homogenous liposome population without post-processing using laminar flow/diffusive mixing, and for reducing waste discharge of the therapeutic or compound to be encapsulated and delivered by the liposomes.

15 Claims, 3 Drawing Sheets

MICROFLUIDIC APPARATUS TO CONTROL LIPOSOME FORMATION

CROSS-REFERENCE TO RELATED APPLICATIONS

This application claims priority to U.S. Provisional Application No. 61/172,806 filed on Apr. 27, 2009 and is a continuation-in-part of U.S. patent application Ser. No. 10/895,366 filed on Jul. 21, 2004.

STATEMENT REGARDING FEDERALLY SPONSORED RESEARCH OR DEVELOPMENT

This invention (NIST Case #09-017) was developed with funds from the National Institute of Standards and Technology.

INCORPORATION BY REFERENCE

This application incorporates by reference U.S. patent application Ser. No. 10/895,366 (the '366 application), filed Jul. 21, 2004, and the following three articles by the inventors of the '366 application: (1) A. Jahn, J. E. Reiner, W. N. Vreeland, D. DeVoe, L. E. Locascio, M. Gaitan, 11*th Annual Nano Science and Technology Institute (NSTI) Nanotech* (2008) (2) Andreas Jahn, Wyatt N. Vreeland, Don L. DeVoe, Laurie E. Locascio, Michael Gaitan, *Langmuir* 23 (11), 6289 (2007); (3) Andreas Jahn, Wyatt N. Vreeland, Don L. DeVoe, Laurie E. Locascio, Michael Gaitan, *J. Am. Chem. Soc.* 126, 2674 (2004). (All non-patent publications incorporated by reference have been included herewith.)

TERMINOLOGY

As used herein, the term "convective mixing interface" refers to an interface at which two fluids are brought together and at which diffusion is possible as the fluids move within a structure.

As used herein, the term "delivery compound" refers to any compound containing or comprising a drug, therapeutic, diagnostic or any other chemical compound or particle which may be encapsulated in a liposome for use in medical or non-medical applications.

As used herein, the term "homogenous liposome populations" means a liposome population with a relative standard size deviation of less than 20%.

As used herein, the term "laminar flow" is a fluid condition of non-turbulent flow. Laminar flow allows for reproducible diffusive mixing and has a Reynolds number of less than 10,000.

As used herein, the term "laminar flow condition" means a condition in which diffusion at a convective mixing interface is possible and at which the controlled assembly of liposomes is possible.

As used herein, the term "liposome" refers to phospholipid molecules assembled in a spherical configuration encapsulating an interior aqueous volume that is segregated from an aqueous exterior. The lipid molecules are not soluble in water but may be dissolved in a solvent.

As used herein, the term "loading efficiency" or "encapsulation efficiency" refers to the quantity of encapsulant captured or contained within a liposome relative to the quantity of encapsulant discharged during a process, and may be expressed herein as a percentage.

As used herein, the term "miscible fluid mixing channel" refers to a channel in which two or more miscible fluids are maintained under laminar flow conditions.

As used herein, the term "pump" refers to any device for raising, compressing, moving or transferring fluids, including conventional pumps and devices relying on gravity and geometric configuration.

As used herein, the term "reaction channel" refers to a channel which includes two or more miscible fluids and a convective mixing interface at which diffusive mixing occurs.

As used herein, the term "viscous shearing" means a horizontal stress created by a difference in viscosity between two immiscible fluids which results in the formation of droplets.

FIELD OF INVENTION

The present invention relates to a microfluidic device to control the amount of delivery compound incorporated in a liposome on a nanometer size scale using laminar flow and miscible fluids, thereby increasing loading efficiency.

BACKGROUND

Figure 1:
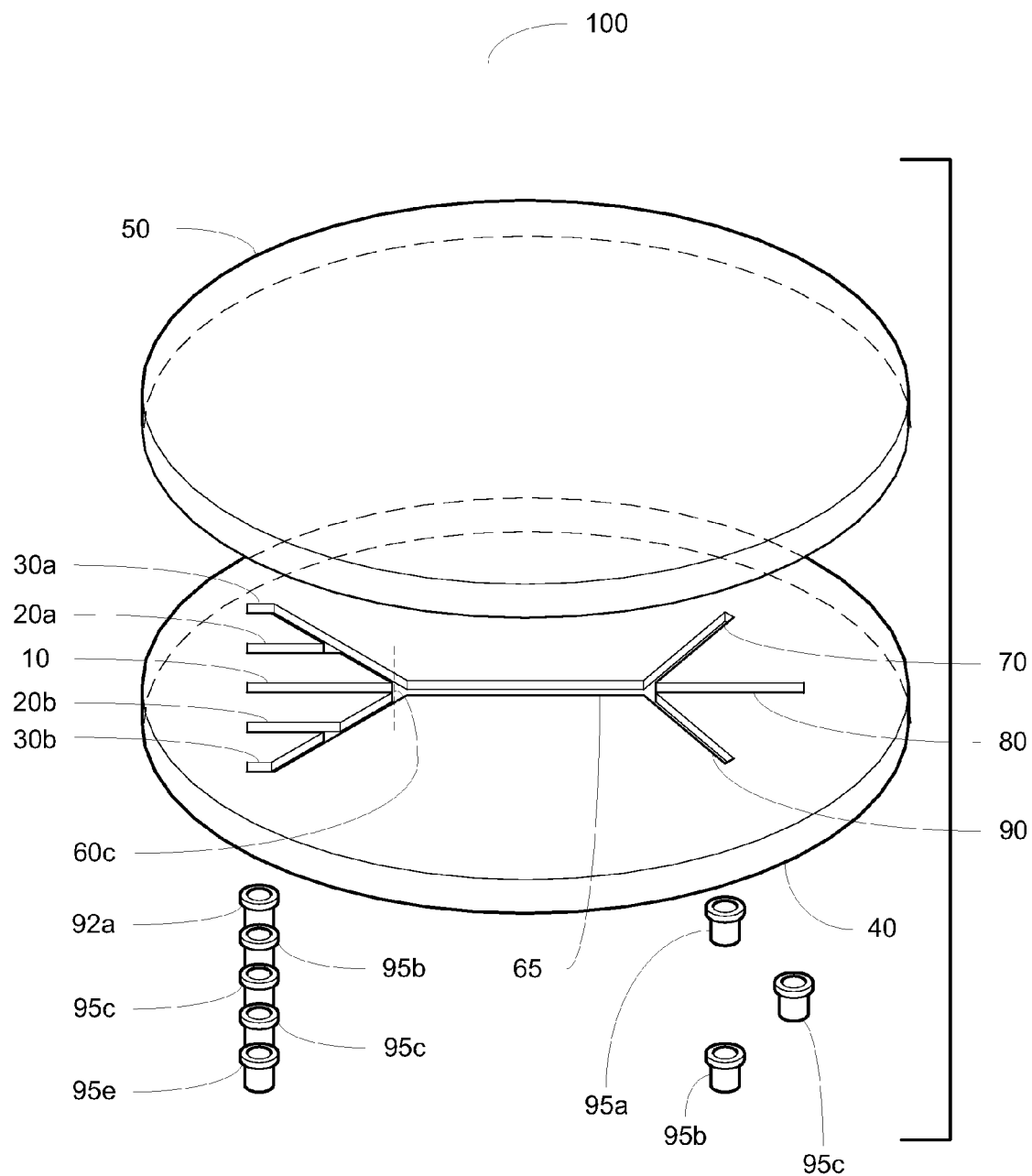
FIG. 1 illustrates a first exemplary embodiment of a microfluidic device for controlling size and loading efficiency of liposomes.

Liposomes are used in a wide variety of medical applications, in which a chemical compound ("delivery compound") is encapsulated in a liposome. Examples of delivery compounds include, but are not limited to, drugs, quantum dots, salts, nutrients, therapeutic agents, proteins, and contrast agents for use in enhanced magnetic resonance imaging and in model systems for the study of biological membranes.

It is desirable to control several aspects of liposome production efficiently: (1) the size of liposomes; (2) the amount of delivery compound encapsulated in each liposome; and (3) the amount of waste of a delivery compound ("loading efficiency"). Increased loading efficiency is particularly important for drug delivery applications as it reduces the amount of the delivery compound that is lost (discharged) during liposome production.

Reducing encapsulant waste through increased loading efficiency can dramatically drive down the commercial cost (and worldwide availability) of drug delivery and result in a profound commercial advantage among competing liposome formation processes. Loading efficiency is accomplished by controlling the stream of encapsulant introduced into a microfluidic device.

There are a number of methods and microfluidic device structures known in the prior art for producing liposomes. However, the size of the liposomes, the amount of delivery compound encapsulated, and the loading efficiency cannot be controlled by these processes. Moreover, processes known in the prior art require the use of costly secondary processes to manage liposome size differentials. The efficiency of some of these methods is often limited by their reliance on viscous shearing and emulsion processes which form liposomes under turbulent flow conditions which are not fully amenable to control.

For example, U.S. Pat. No. 7,595,195 (Lee '195) teaches the use of a microfluidic device for creating liposomes using an emulsion process.

The microfluidic device taught by Lee '195 is specifically used to create liposomes using controlled viscous shearing of oil-water emulsions under turbulent flow conditions (using immiscible fluids) to create liposomes.

Lee '195 teaches a device having a three channel structure. The three channel structure and method utilized by Lee '195 teaches introduction of encapsulent carried in a water stream into either the center channel or into the two outer channels.

The method disclosed by Lee '195, however, is unable to achieve formation of droplets smaller than 1 µm. For example, the process utilized by Lee '195 does not result in liposomes in the 100 to 300 nm range in a single process. Lee requires secondary processes to manage size differentials in the liposome population, including but not limited to sonication and membrane extrusion.

The size of liposomes is critical to the accurate delivery of drugs and other delivery compounds, therapeutic efficiency, and cellular uptake.

It is desirable to have a microfluidic apparatus and method for creating liposomes which (1) does not rely on the use of viscous shearing (turbulent flow) to produce liposomes; (2) does not require significant post-assembly and post-processing to create homogenous liposome populations; (3) can produce liposomes on a nanometer scale; and (4) can minimize the rate of discharge of the costly encapsulation compound.

SUMMARY OF THE INVENTION

The present invention is a method for tailoring the size and size distribution of nanometer scale liposomes, controlling the concentration of molecules encapsulated in the liposomes, and controlling discharge (waste) of costly delivery compounds. The present microfluidic apparatus utilizes a plurality of inlet and outlet channels and fluid interconnect components. The desired channel structure is etched onto a silicon wafer and sealed by a glass wafer.

The microfluidic apparatus has at least one lipid channel through which a lipid solution flows, at least one delivery compound channel through which a delivery compound stream flows, at least one buffer channel through which a buffer stream flows, and a reaction channel which has a convective diffusive mixing interface. The microfluidic apparatus further includes at least one liposome outlet channel and at least two waste channels.

In various embodiments, channels have a width ranging from 10 to 100 µm, depending on the viscosity of the fluids, and it is contemplated that the size range of the channels may be on the order of 0.1 to 1000 µm.

One or more so fluid streams, including a lipid stream, delivery compound streams, and buffer streams, are infused with a syringe pump or any other type of pump known in the art adapted to infuse fluids into a microfluidic apparatus.

The apparatus maintains laminar flow allowing for liposome formation by diffusive mixing in a reaction channel having a convective mixing interface. Using laminar flow (rather than turbulent flow) allows production of a homogenous liposome population eliminating the need for post-processing of the liposomes to account for size differentials.

The loading efficiency can be controlled by adjusting the volumetric flow rate of the buffer stream through the buffer channel and the delivery compound stream through the delivery compound channel. The concentration of the delivery compound encapsulated can be controlled by adjusting the starting concentration of the delivery compound and the length of the delivery compound channel.

DETAILED DESCRIPTION OF EXEMPLARY EMBODIMENTS

For the purpose of promoting an understanding of the present invention, references are made in the text to exemplary embodiments of an apparatus and method for controlling the size and size distribution of liposomes and the encapsulation efficiency, only some of which are described herein. It should be understood that no limitations on the scope of the invention are intended by describing these exemplary embodiments. One of ordinary skill in the art will readily appreciate that alternate but functionally equivalent materials, concentrations and microfluidic devices may be used. The inclusion of additional elements may be deemed readily apparent and obvious to It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

FIG. 1 illustrates a first exemplary embodiment of microfluidic apparatus 100, which enables laminar flow conditions and is configured in a manner for controlling size encapsulation efficiency of liposomes. Microfluidic apparatus 100 accomplishes liposome formation using miscible fluid compounds which are diffusively mixed under laminar flow conditions.

In the exemplary embodiment illustrated in FIG. 1, microfluidic apparatus 100 includes five inlet channels 10, 20a, 20b, 30a, 30b, reaction channel 65 and outlet channels 70, 80, 90. The inlet channels include lipid channel 10, delivery compound channels 20a and 20b, and buffer compound channels 30a and 30b. Other embodiments may include more or few inlet and outlet channels.

The embodiment shown, channels 10, 20a, 20b, 30a, 30b, 65, 70, 80, 90 are etched into silicon wafer 40 and sealed by glass wafer 50.

Visible in FIG. 1 are fluid interconnect components 92a, 92b, 92c, 92d, 92e, 95a, 95b, 95c, which are fluid ports affixed to silicon wafer 40, used to add or remove solutions from the channels.

In the embodiment shown, fluid interconnect components 92a, 92b, 92c, 92d, 92e, 95a, 95b, 95c are components adapted to receive fluids actuated by a pump or capillary structure known in the art. In the embodiment shown, fluid interconnect components 92a, 92b, 92c, 92d, 92e, 95a, 95b, 95c are commercially available NanoPort™ Assemblies (Upchurch Scientific Oak Harbor, Calif.), but can be any equivalent fluid interconnect components known in the art.

Lipid stream channel 10 is adapted to receive a lipid mixture dissolved in an aqueous-miscible solvent. Other embodiments of the invention may include more lipid stream channels. In the embodiment shown, the lipid stream is a lipid is dissolved in isopropyl alcohol (IPA), but in other embodiments, the lipid maybe dissolved in ethanol, methanol, or another non-polar solvent that is compatible with the lipid and is capable of diffusing and mixing with water, and may be of varying concentrations.

Delivery compound stream channels 20a, 20b are adapted to receive a delivery compound (i.e., the compound that is to be encapsulated in the liposomes) dissolved in water. In various embodiments, the delivery compound may be a drug, dye, quantum dot, salt, nutrients or any other compound or particle. The delivery compound stream is added to channels 20a, 20b, which are located directly on either side of solvent stream channel 10.

Buffer stream channels 30a, 30b are adapted to receive a buffer stream comprised of an aqueous buffer solution, such as phosphate buffered saline (PBS), phosphate buffer, TRIS buffer, HEPES buffer or another type of buffer that is miscible with the solvent stream and delivery compound stream. In the embodiment shown, PBS is used as the buffer stream.

Other embodiments of the invention may include more or fewer buffer channels. For example, the '366 patent contemplates a three channel structure which omits buffer channels 30a, 30b.

The solutions in the solvent stream, the delivery compound streams and the buffer streams are all comprised of miscible fluids.

In the embodiment shown, channels 10, 20a, 20b, 30a, 30b, 65, 70, 80, 90 are configured to allow for laminar flow and diffusive mixing of the lipid stream, delivery compound streams, and buffer streams. Channels between 0.1 µm and 500 µm in width will support and continuously maintain laminar flow of fluids. In the embodiment shown, channels 10, 20a, 20b, 30a, 30b, 65, 70, 80, 90 have a rectangular cross section with a depth of 100 µm and width of 42 µm or 64 µm.

In the embodiment shown, lipid stream channel 10 located between delivery compound stream channels 20a, 20b. Channel 30a intersects with channel 20a at convective diffusive mixing interface 60a (see FIG. 2) and channel 30b intersects with channel 20b at convective diffusive mixing interface 60b (see FIG. 2) resulting in the delivery compound streams (channels 20a, 20b) mixing with and flowing into buffer streams (channels 30a, 30b). In the embodiment shown, delivery compound stream channels 20 and buffer stream channels 30 intersect at a 45 degree angle (see FIG. 2), but in various embodiments the angle of intersection may be 30 to 150 degrees.

Channels 30a, 30b then intersect channel 10 at convective diffusive mixing interface 60c. Convective diffusive mixing interface 60c moves through reaction channel 65 as the solutions diffusely mix as they convect through reaction channel 65.

At convective diffusive mixing interface 60c, lipid stream 10 is diluted by buffer streams 30a, 30b resulting in an alcohol concentration that is no longer high enough for the lipids to remain solvated causing the lipids to self-assemble into liposomes. When the lipids self-assemble, they encapsulate the compound from delivery compound streams 20a, 20b.

Mixing at convective diffusive mixing interfaces 60a, 60b, 60c occur only by convection and diffusion because all streams are miscible.

When laminar flow conditions are maintained, phospholipid molecules spontaneously reassemble into liposomes around the compound from delivery compound stream channels 20a, 20b. It is a critical aspect of microfluidic apparatus 100 that laminar flow conditions are maintained in microfluidic channels 10, 20a, 20b, 30a, 30b, 65, 70, 80, 90 of microfluidic apparatus 100.

The state of laminar flow enables convective diffusion at convective diffusive mixing interfaces 60a, 60b, 60c controlling liposome formation and resulting in a homogenous liposome population. Both laminar flow and the formation of a convective diffusive mixing interface are critical. The liposome population is discharged from channel 80 and excess buffer is discharged from channels 70, 90.

In the exemplary embodiment, microfluidic apparatus 100 produces liposomes having a diameter ranging from 40 to 300 nm with a relative standard deviation of less than 10% for liposomes having a diameter smaller than 80 nm and a The ability to produce a homogenous liposome population on a nanometer scale is a direct result of laminar flow conditions which enables diffusive mixing. Devices and method using turbulent flow and viscous shearing are unable to achieve a homogenous liposome population with liposomes on the nanometer size scale.

Utilizing microfluidic apparatus 100 and the method disclosed in the '366 application, phospholipid molecules spontaneously reassemble into a sphere around the encapsulant without the use of a viscous shearing process in a controlled manner to create a homogeneous liposome population which does not require post processing procedures (e.g., sonication, membrane extrusion) to accommodate size differentials in the liposome population.

Using the method of the '366 patent, the vesicle size and size distribution can be varied by adjusting the volumetric flow rate ratio of the delivery compound streams (channels 20a, 20b) and the buffer streams (channels 30a, 30b). The amount of delivery compound in the delivery compound streams is adjusted in two ways. First, by adjusting the volumetric flow rate ratio of the delivery compound streams and the buffer streams. Reducing the volume/flow rate of the delivery compound streams 20a, 20b and increasing the volume/flow rate of the buffer streams 30a, 30b results in a thin stream of the delivery compound and less waste when encapsulated within the liposome. The amount of delivery compound in the delivery compound streams can also be adjusted by changing the concentration of the delivery compound, i.e., by controlling the number of molecules of delivery compound in delivery compound streams. It is contemplated that liposomes containing one or a few molecules of delivery compound can be created in this manner, as well as liposomes containing a greater amount of delivery compound.

It is contemplated that hydrodynamic focusing of fluid streams will allow for fast and controlled mixing in a microfluidic format under a variety of conditions with the benefit of reduced sample consumption. In an exemplary embodiment, the flow conditions in the microchannels are laminar with a Reynolds numbers of approximately 20.

In the exemplary embodiment shown, the VFR is on the order of 100 µl per minute. However, the VFR will vary depending on the length, width and depth of the channels and may be as low as 0.1 µl per minute and as high as 1 ml per minute.

Using microfluidic apparatus 100 and the method disclosed in the '366 application, the liposome size is tunable over a mean diameter of 40 nm to 300 nm by adjusting the aqueous to solvent volumetric flow rate ratio.

In various embodiments, the length of channels 10, 20a, 20b, 30a, 30b may vary between 0.01 mm and several hundred millimeters and the length will vary depending on channel width. The wider the channel is, the longer it has to be to allow for complete mixing of the solvent stream with the adjacent buffer streams.

FIG. 1 illustrates an exemplary embodiment of microfluidic apparatus 100 in which lipid stream channel 10 is 5 mm long and 10 µm wide, however, in other embodiments lipid stream channel 10 may be up to a few centimeters (1 to 10) or up to 500 μm wide. Other channels will have proportionate dimensions.

Channel depth is dependent on the fabrication method, type of substrate and material used. In the embodiment shown silicon wafers are used, and channel depth is 180 μm.

In various embodiments, performance may be improved by deepening the channels (e.g., to a depth of several millimeters to 1 in).

In various embodiments, the cross section of channels 10, 20a, 20b, 30a, 30b, 65, 70, 80, 90 may vary (e.g., may be trapezoidal, rectangular, tubular, circular or any other configuration known in the art). Cross section and depth are about the same or less than the channel width.

It is contemplated that the channel depth may be more than 5 times deeper than the channel width. In the embodiment shown, the ratio of channel depth to channel width is 2 to 3.6.

The distance (length) from the start of delivery compound channels 20a, 20b to convective diffusive mixing interfaces 60a, 60b and from convective diffusive mixing interfaces 60a, 60b to convective diffusing mixing interface 60c are determined by the structural requirements for achieving and maintaining laminar flow, the application, and the desired diffusion of the delivery compound prior to encapsulation. The greater the distance from the start of channels 20a, 20b to convective diffusive mixing interface 60c, the more diffusive mixing that occurs between delivery compound streams (channels 20a, 20b) and the buffer (channels 30a, 30b). If more dilution of the delivery compound is desired, the start of delivery compound channels 20a, 20b should be located further from convective diffusive mixing interfaces 60a, 60b (i.e., the length of delivery compound channels 20a, 20b should be increased) giving the delivery compound more time to diffuse.

The higher the Reynolds number (e.g., from 2 to 20), the more important the angles at the which the channels intersect may be, that is, inertia becomes more important and angles $\theta_2$, $\theta_3$ (FIG. 2), that is, the angle between channels 30a, 30b and channel 10, be less or equal 90 degrees.

Figure 2:
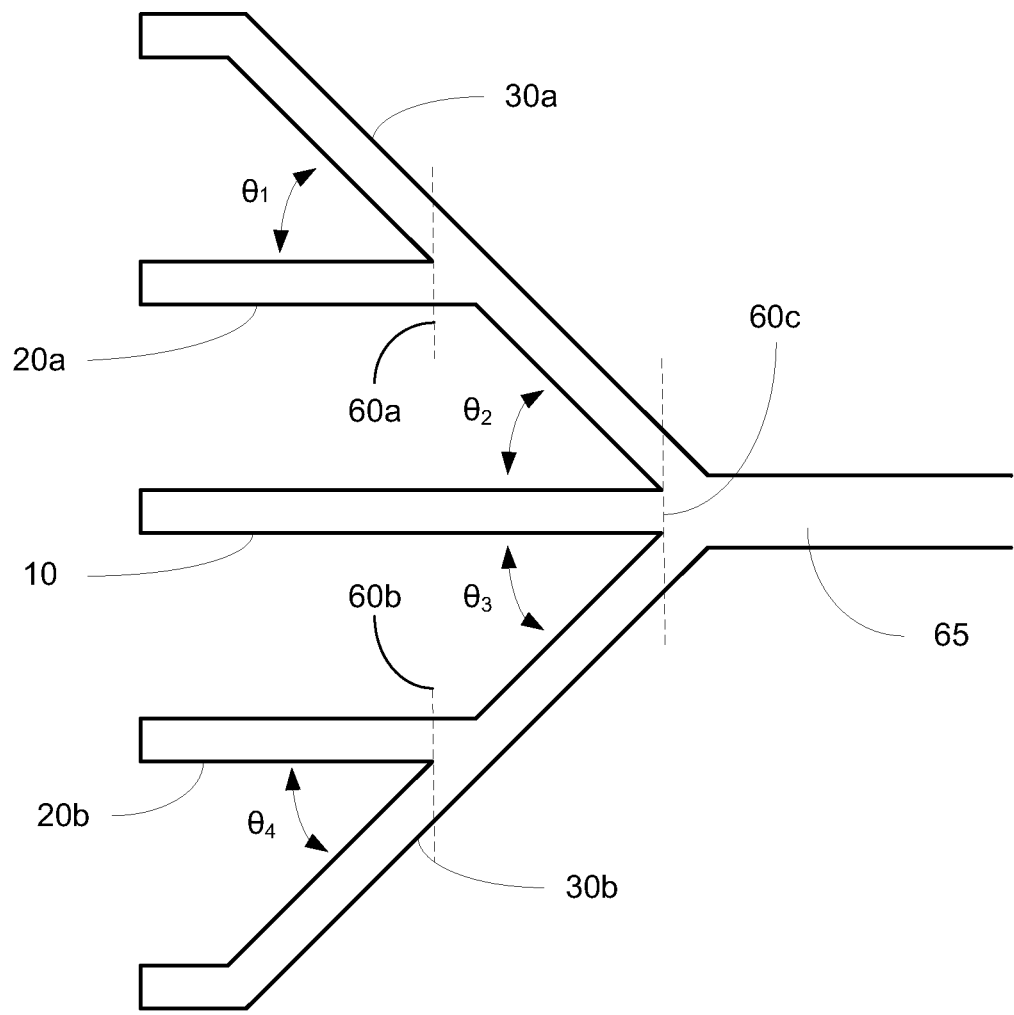
FIG. 2 illustrates an isolated view of the intersection of the inlet channels of an exemplary embodiment of a microfluidic apparatus for controlling size and loading efficiency of liposomes.

FIG. 2 illustrates an isolated view of the intersection of inlet channels 10, 20a, 20b, 30a, 30b of an exemplary embodiment of microfluidic apparatus 100 for controlling size and encapsulation efficiency of liposomes.

In the embodiment shown angels $\theta_1$, $\theta_2$, $\theta_3$ and $\theta_4$ are 45° angles, but may vary between 30° and 150° and still support laminar flow conditions.

Figure 3:
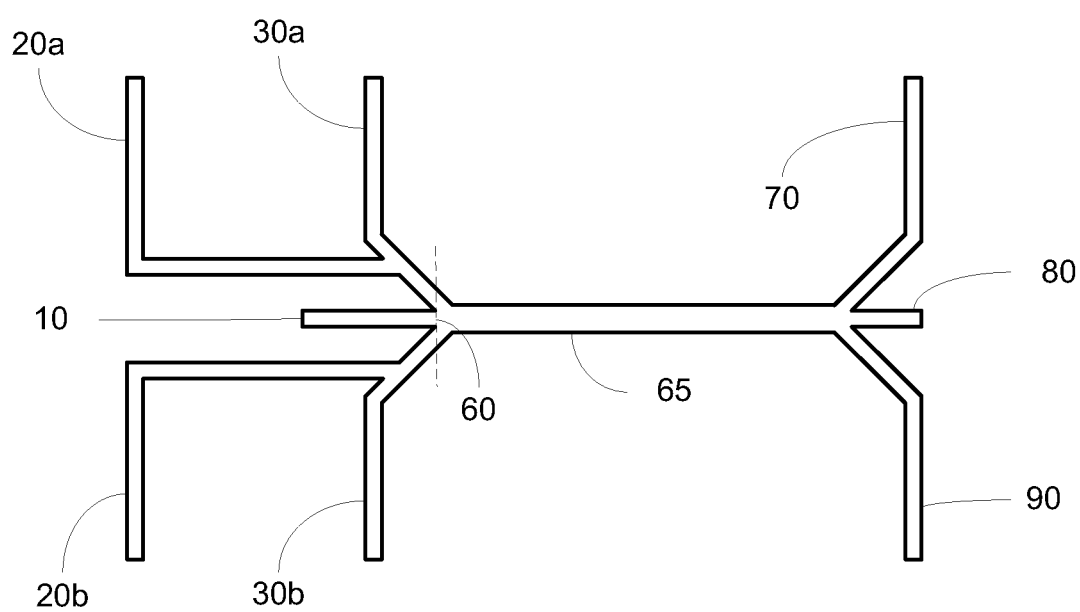
FIG. 3 illustrates a second exemplary embodiment of a microfluidic apparatus for controlling size and loading efficiency of liposomes.

FIG. 3a illustrates a second exemplary embodiment of microfluidic apparatus 100 for controlling size, lamellarity and encapsulation efficiency of liposomes.

What is claimed is:

1. A microfluidic apparatus for producing laminar flow for the formation of liposomes of uniform size having a mean diameter of 40 nanometers to 300 nanometers with a standard deviation of less than 10% for liposomes having a diameter smaller than 80 nm, comprised of:
    a substrate including
        a lipid channel through which a miscible lipid stream flows
            wherein said lipid channel having a channel depth to width ratio of greater than 2 to 1 and;
            wherein said lipid channel has a volumetric flow rate between 0.1 microliter/minute and 1 milliliter/minute resulting in a non-overlapping flow stream;
        a laminar flow delivery compound channel having a channel depth to width ratio of greater than 2 to 1 and through which a miscible delivery compound stream flows;
        a laminar flow buffer channel having a channel depth to width ratio of greater than 2 to 1 and through which a miscible buffer stream flows;
        a laminar flow reaction which includes a convective diffusing mixing interface;
        wherein loading efficiency may be varied by adjusting the ratio of the volumetric flow rate through said buffer channel and
            said delivery compound channel;
        at least one liposome outlet channel; and
        at least one waste channel;
        wherein said lipid channel, said delivery compound channel, said buffer channel, said liposome outlet channel, and said at least one waste channel are of dimensions that support laminar flow; and
    a sealing component bonded to the top surface of said substrate.

2. The apparatus of claim 1 wherein said at least one buffer channel and said at least one delivery compound channel intersect at a second convective diffusive mixing interface to form a miscible fluid mixing channel.

3. The apparatus of claim 2 wherein said at least one buffer channel and said at least one delivery compound channel intersect at an angle sufficient to maintain laminar flow.

4. The apparatus of claim 2 wherein said at least one buffer channel and said at least one delivery compound channel intersect at an angle of 30 to 150 degrees.

5. The apparatus of claim 2 wherein said miscible fluid mixing channel intersects said at least one lipid channel to form said reaction channel.

6. The apparatus of claim 2 wherein said miscible fluid mixing channel intersects said at least one lipid channel at an angle sufficient to maintain laminar flow.

7. The apparatus of claim 2 wherein said miscible fluid mixing channel intersects said at least one lipid channel at an angle of 30 to 150 degrees.

8. The apparatus of claim 1 wherein said at least one lipid channel has a width of 0.1 to 500 micrometers and a length of 1 to 100 millimeters.

9. The apparatus of claim 1 wherein said at least one delivery compound channel has a width of 0.1 to 500 micrometers and a length of 1 to 100 millimeters.

10. The apparatus of claim 1 wherein said at least one buffer channel has a width of 0.1 to 500 micrometers and a length of 1 to 100 millimeters.

11. The apparatus of claim 1 wherein the volumetric flow rate of said lipid stream through said at least one lipid channel is 100 microliters per minute.

12. The apparatus of claim 1 wherein loading efficiency may be varied by adjusting the length of said at least one delivery compound channel.

13. A method of controlling the loading efficiency of the microfluidic apparatus of claim 1 comprising;
    adjusting the volumetric flow rate of a buffer stream through a buffer channel; and
    adjusting the volumetric flow rate of a delivery compound stream through a delivery compound channel.

14. The method of claim 13 which further includes the step of controlling the concentration of a delivery compound in said delivery compound stream.

15. The method of claim 14 wherein said concentration of said delivery compound is controlled by adjusting the length of said delivery compound channel.

* * * * *